United States Patent [19]

Liegner

[11] Patent Number: 4,495,945
[45] Date of Patent: Jan. 29, 1985

[54] BITE BLOCK

[76] Inventor: Kenneth B. Liegner, 315 Bear Ridge Rd., Pleasantville, N.Y. 10570

[21] Appl. No.: 362,524

[22] Filed: Mar. 29, 1982

[51] Int. Cl.³ .............................................. A61M 16/00
[52] U.S. Cl. ................................. 128/200.26; 128/136
[58] Field of Search ...................... 128/200.26, 207.14, 128/207.15, 207.17, 136, 4, 10

[56] References Cited

U.S. PATENT DOCUMENTS 2,669,988  2/1954  Carpenter ........................... 128/136
3,126,002  3/1964  Owens ................................. 128/136
3,768,465  10/1973  Helmer ............................... 128/136
4,090,518  5/1978  Elam ............................... 128/207.15

Primary Examiner—Henry J. Recla
Attorney, Agent, or Firm—Kane, Dalsimer, Kane, Sullivan and Kurucz

[57] ABSTRACT

Disclosure is made herein of a bite block which is usefully employed in conjunction with endoscopy, bronchoscopy, endotracheal intubation and like medical-surgical procedures.

2 Claims, 3 Drawing Figures

BITE BLOCK

BACKGROUND OF THE INVENTION

1. Field of the Invention

The invention relates to a bite block and more particularly relates to a bite block which is usefully employed in conjunction with endoscopy, bronchoscopy, endotracheal intubation and like medical-surgical procedures.

2. Brief Description of the Prior Art

Not infrequently, patients in hospital emergency rooms and intensive care units require endotracheal intubation for mechanical ventilatory support during acute respiratory failure. Endotracheal tubes are formed by cylindrical pliable plastic, ranging in internal diameter from 4 to 9 millimeters.

Such patients are often unresponsive initially, but frequently struggle against both the endotracheal tube and the ventilator as their condition is stabilized and improves. Often they bite down with their teeth against the endotracheal tube such that necessary suctioning of pulmonary secretions is made difficult or impossible or occasionally the endotracheal tube or its pilot balloon is bitten in two, leading to potentially life threatening loss of control of the airway.

Small bite blocks or oropharyngeal airways that are now commercially available are unstable in maintaining position and are readily displaced by the patient's tongue or jaw movements. The present invention provides a bite block molded to fit the teeth, gums, jaw, palate, and lips in such a way that expulsion by the patient is unlikely. Structure is provided to permit stabilization of the endotracheal tube and allow catheter suctioning of oropharyngeal secretions or regurgitated gastric contents and drainage of gastric contents. The bite block prevents the patient from biting down on the endotracheal tube or suction catheters.

Other uses of the invention include assisting fiberoptic endoscopy and prevent the patient from biting down on the scopes thereby preventing costly damage to the fiberoptic components.

SUMMARY OF THE INVENTION

The invention comprises a bite block which is useful in conjunction with endoscopy, bronchoscopy, endotracheal intubation and like procedures, which comprises;

(a) a "U" shaped plate having first and second ends, each end being at the terminus of a separate upright leg of the "U", said plate comprising a plate body intermediate between and joining the first and second ends, said plate body having (1) an upper surface delineated by the ends and inner and outer marginal zones;
(2) a lower surface delineated by the ends and inner and outer marginal zones;
(3) an inner side delineated by the ends and upper and lower marginal zones; and
(4) an outer side delineated by the ends and upper and lower marginal zones;
  the inner side joining at its upper marginal zone with the inner marginal zone of the upper surface and at its lower marginal zone with the inner marginal zone of the lower surface;
  the outer side joining at its upper marginal zone with the outer marginal zone of the upper surface and at its lower marginal zone with the outer marginal zone of the lower surface;
said plate body further having
(5) a groove in the upper surface, between the inner and the outer marginal zones of the upper surface adapted by size and configuration to receive therein the upper teeth (or, in the absence of teeth, the associated gums) of a human being; and
(6) a groove in the lower surface, between the inner and the outer marginal zones of the lower surface, adapted by size and configuration to receive therein the lower teeth (or in the absence of teeth, the associated gums) of a human being; whereby when the plate is inserted into the vestibulum oris of a human being, the upper teeth or gums will be received in the upper surface groove and held apart by the plate body from the lower teeth or gums which are received in the lower surface groove;

(b) a ridge on the outer side of the plate body, positioned between the upper and the lower marginal zones of the outer side at the bottom of the "U" and extending outwardly from the outer side to a ridge terminus;

(c) an upper flange on and projecting upwardly from the ridge terminus, providing an open space between the upper flange, the upper marginal zone of the outer side and the upper side of the ridge, said space being of a size and configuration to receive the labium superiori oris of a human in sealing engagement with said flange, outer side and ridge;

(d) a lower flange on and projecting downwardly from the ridge terminus, providing an open space between the lower flange, the lower marginal zone of the outer side and the lower side of the ridge, said space being of a size and configuration to receive the labium inferiori oris of a human in sealing engagement with said lower flange, outer side and ridge;

(e) a bore traversing the plate and ridge at the bottom of the "U", communicating between the inner side of the plate and the ridge terminus, said bore being of a dimension to pass an endoscope, a bronchoscope, an endotracheal tube or the like; and (f) optionally at least one additional bore traversing the plate and ridge adjacent the bottom of the "U", communicating between the inner side of the plate and the ridge terminus, said additional bore being of a dimension to pass an oropharyngeal endotracheal, or orogastric tube; said bite block being of a size and configuration permitting insertion of the "U" shaped plate component into the vestibulum oris of a human as described above and whereby the bridge and flange components sealingly engage the labium oris so that the oral cavity is restricted to communication to the exterior through the bore and optional bore.

DETAILED DESCRIPTION OF THE PREFERRED EMBODIMENTS OF THE INVENTION

Figure 1:
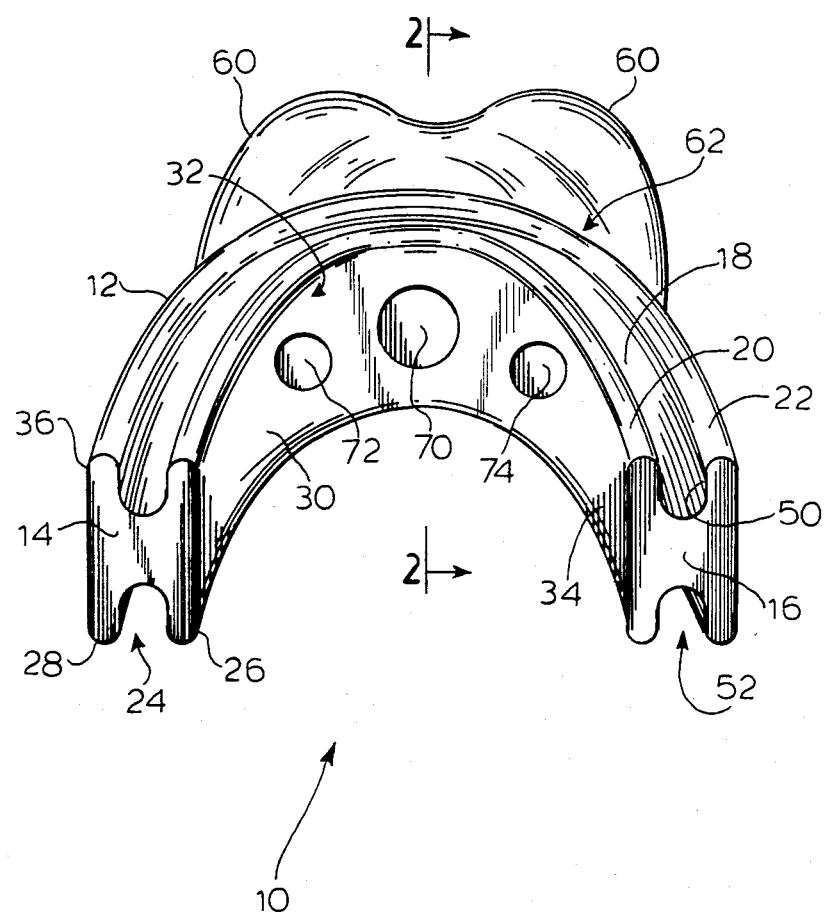
FIG. 1 is an elevational view of an embodiment bite block of the invention, showing the inner or posterior structure.

Referring first to FIG. 1, there is seen an elevational view of an embodiment bite block 10 of the invention, showing the inner or posterior structure. The bite block 10 is a generally "U" shaped plate 12 having a first end 14 and a second end 16. Each of the ends 14, 16 are at the terminus of a separate upright leg of the "U", and represent the end of plate 12 which will be inserted first into the vestibulum oris of a human being during use. The plate 12, intermediate between and joining ends 14, 16, has an upper surface 18 delineated by the ends and inner marginal zone 20 and outer marginal zone 22. The lower surface 24 of plate 12 is also delineated by the ends 14, 16 and by an inner margin 26 and an outer margin 28. The plate 12 is also bounded by an inner side 30 which has an upper 32 and a lower 34 marginal zone. An outer side 36 of the plate 12 is delineated by corresponding upper and lower marginal zones 38, 40 respectively (not seen in FIG. 1; see FIG. 3). The outer side 36 joins at the upper marginal zone 38 with the outer marginal zone 22 of upper surface 18 and at the lower marginal zone 40 with the outer marginal zone 28 of lower surface 24. The inner side 30 joins at its upper marginal zone 32 with the inner marginal zone 20 of upper surface 18 and at its lower margin zone 34 with the inner marginal zone 26 of lower surface 24.

The plate 12 further has a groove 50 in the upper surface 18 between the inner and outer marginal zones 20, 22 of the upper surface 18, said groove 50 being adapted by size and configuration to receive therein the upper teeth, or in the absence of teeth, the associated gums of a human being. A similar groove 52 is in the lower surface 24, between inner and outer marginal zones 26, 28 of the lower surface 24. The groove 52, like groove 50 is adapted by size and configuration to receive therein the lower teeth or associated gums of a human being when plate 12 is inserted in the vestibulum oris of the human being. When the plate 12 is so inserted, the upper teeth or gums of the human being will be received in the upper surface groove 50 and held apart by the plate body from the lower teeth or gums which are received in the lower surface 24 groove 52.

Figure 2:
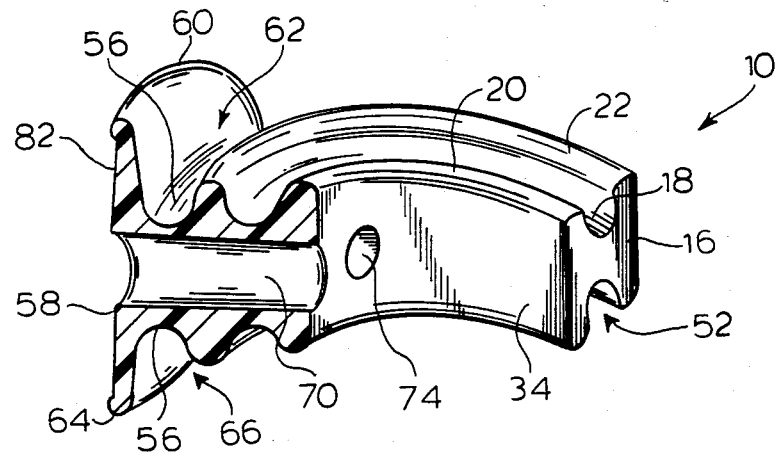
FIG. 2 is a cross-sectional view along lines 2—2 of FIG. 1.

Referring now to FIG. 2, there is seen a cross-sectional side elevation along lines 2—2 of FIG. 1. As shown in the FIG. 2, there is a ridge 56 on the outer side 36 of plate 12, positioned between the upper outside marginal zone 38 and the lower outside marginal zone 40, at the bottom of the "U" and extending outwardly from the outer side 36 to a ridge terminus 58. An upper flange 60 on and projecting upwardly from the ridge terminus 58 provides an open space 62 between the upper flange 60 and the upper marginal zone 38 of the outer side 36 and the upper side of ridge 56. The space 62 is of a size and configuration to receive the labium superiori oris of a human in sealing engagement with said flange 60, outer side 36 and ridge 56. A lower flange 64 on and projecting downwardly from the ridge terminus 58 provides an open space 66 between the lower flange 64, the lower marginal zone 40 of the outer side 36 and the lower side of the ridge 56. Space 66 is of a size and configuration to receive the labium inferiori oris of a human in sealing engagement with said lower flange 64, outer side 36 and ridge 56. A bore 70 traverses plate 12 and ridge 56 at the bottom of the "U", communicating between the inner side 30 of plate 12 and the ridge terminus 58, the bore 70 being of a dimension to pass an endoscope, a bronchoscope, an endotracheal tube or the like. In the preferred embodiment of bite block 10, there are additionally bores 72 and 74 traversing the body of plate 12 and ridge 56 at the bottom of the "U", communicating between the inner side 30 of plate 12 and the ridge terminus 58. The bores 72, 74 are of a dimension to pass endotracheal, oropharyngeal, or orogastric tubes and also provide airways into the oral cavity of a patient when the bite block 10 is inserted therein. The entire bite block 10 is of a size and configuration permitting its use by insertion of ends 14, 16 into the mouth of a human as described above, leaving the ridge 56 and flanges 60, 64 external to the mouth. When bite block 10 is so inserted into the vestibulum oris of a patient, the ridge 56 and flanges 60, 64 cooperate to sealingly engage the labium oris so that the oral cavity of the patient is restricted in communication to the exterior, through the bores 70, 72 and 74. The bite block 10 may be fabricated in a range of standard sizes, selected to fit a range of humans, i.e.; children through adults.

As is readily apparent in FIGS. 1 and 2, grooves 50 and 52 subtend an acute angle in relation to one another, its apex directed towards the back of the "U". Thus when in place in a human mouth such structure maintains the jaws in a widely open position necessary for the intended uses of the bite block.

Figure 3:
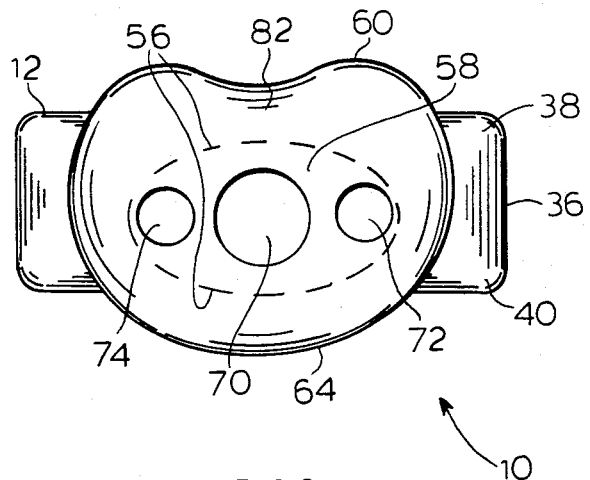
FIG. 3 is a front view of the embodiment of FIG. 1.

FIG. 3 is a front view of the embodiment bite block 10 shown in FIG. 1 and shows further details of the bite block 10. The front surface 82 on terminus 58 may be used to hold an adhesive tape, for securing tubes passing through the bores 70, 72 or 74. A length of such tape passing around the back of the patient's neck and adhering in front to surface 82 would prevent voluntary expulsion of bite block 10.

The bite block 10 is employed when desired by insertion into the vestibulum oris of a human being. Secured in place by the patient's natural reflex to bite down on it, the patient is prevented from injury to self by the biting reflex. Since the bite block 10 fully conforms to the shape of the maxillary and mandibular arcades, it will not shift in position and is securely maintained in the vestibulum oris. The bite block 10 is stable in regard to movement and comfortable to the wearer. While stably maintained in place, such medical-surgical procedures as endoscopy or bronchoscopy, and the like may be carried out by insertion of the appropriate instrument through the bore hole 70. The proximal end of a previously placed endotracheal tube may be passed through bores 70, 72 or 74 as the bite block is inserted. When required, oral-pharyngeal or gastric suctioning of natural secretions may be carried out through the bores 72, 74. All of these procedures may be carried out without interference from the patient biting down upon the instrument, tubing or the like. Upon termination of a particular procedure, the bite block may be maintained in place to function as an airway and/or it may be removed as desired.

The bite block 10 may be fabricated from any conventional materials, preferably a polymeric resin which has sufficient strength to resist a patient biting through but which is resilient enough that injury to the patient's teeth and/or gums does not occur. Preferably, the bite block 10 is fabricated from polyethylene, polypropylene and like polymeric resins.

In one embodiment of the invention, the bite block 10 may be fabricated from an ethylene-vinyl acetate or like material which softens at a temperature of about 45° to 100° C. This bite block 10 may be made to conform and mold to the exact configuration of a particular patient's maxillary and mandibular arches, including the teeth and gums, by softening the bite block 10 in a hot water immersion. After removing the bite block 10 with its softened ethylene-vinyl acetate surface, from the immersion, it may be inserted into the vestibulum oris of a particular human individual (allowing it to cool first as necessary to avoid a burn injury to the individual). The human then brings his jaws together in a normal closing manner to displace softened thermoplastic material. In this way, the grooves 50 and 52 are made to conform to the anatomical structure of the individual's teeth and/or gums. The bite block 10 is then removed and allowed to reharden. It may then be used subsequently in the above described medical-surgical procedures wherein the bite block 10 will fit perfectly in the vestibulum oris of the individual patient.

What is claimed is:

1. A bite block which is useful in conjunction with endoscopy, bronchoscopy, endotracheal intubation and like procedures, which comprises;
   (a) a "U" shaped plate having first and second ends, each end being at the terminus of a separate leg of the "U" joined by a bridging section, said plate comprising a plate body intermediate between and joining the first and second ends, said plate body being fabricated from a polymeric resin having sufficient strength to resist biting through but which is resilient enough that injury to the biter's teeth and gums does not occur, said "U" shape plate having (1) an upper surface delineated by the ends and inner and outer marginal zones; (2) a lower surface delineated by the ends and inner and outer marginal zones; (3) an inner side delineated by the ends and upper and lower marginal zones; and (4) an outer side delineated by the ends and upper and lower marginal zones; the inner side joining at its upper marginal zone with the inner marginal zone of the upper surface and at its lower marginal zone with the inner marginal zone of the lower surface; the outer side joining at its upper marginal zone with the outer marginal one of the upper surface and at its lower marginal zone with the outer marginal zone of the lower surface;
   (b) a ridge on the outer side of the plate body, positioned between the upper and the lower marginal zones of the outer side at the bridging section of the "U" and extending outwardly from the outer side to a ridge terminus;
   (c) an upper flange on and projecting upwardly from the ridge terminus, providing an open space between the upper flange, the upper marginal zone of the outer side and the upper side of the ridge, said space being of a size and configuration to receive the labium superiori oris of a human in sealing engagement with said flange, outer side and ridge;
   (d) a lower flange on and projecting downwardly from the ridge terminus, providing an open space between the lower flange, the lower marginal zone of the outer side and the lower side of the ridge, said space being of a size and configuration to receive the labium inferiori oris of a human in sealing engagement with said lower flange, outer side and ridge;
   (e) an open bore traversing the plate and ridge at the bridging section of the "U", communicating between the inner side of the plate and the ridge terminus, said bore being of a dimension to pass an endoscope, a bronchoscope, an endotracheal tube or the like therethrough;
   (f) said plate body further having
      (1) a groove in the upper surface extending from said first end to said second end and between the inner and the outer marginal zones of the upper surface adapted by size and configuration to receive therein the upper teeth (or, in the absence of teeth, the associated gums) of a human being; and
      (2) a groove in the lower surface extending from said first end to said second end and between the inner and the outer marginal zones of the lower surface, adapted by size and configuration to receive therein the lower teeth (or in the absence of teeth, the associated gums) of a human being; whereby when the plate is inserted into the vestibulum oris of a human being, the upper teeth or gums will be received in the upper surface groove and held apart by the plate body from the lower teeth or gums which are received in the lower surface groove; said groove in the upper surface and said groove in the lower surface each defining a smooth inside surface and subtending an acute angle in relation to each other, the apex of said angle being directed toward the first and second ends of the "U";
   (g) at least one additional open bore traversing the plate and ridge adjacent to the bridging section of the "U", communicating between the inner side of the plate and the ridge terminus, said additional bore being of a dimension to pass an endotracheal tube, oropharyngeal or orogastric tube; said bite block being of a size and configuration permitting insertion of the "U" shaped plate component into the vertibulum oris of a human as described above and whereby the ridge and flange components sealingly engage the labium oris so that the oral cavity is restricted to communication to the exterior through the bore and optional bores.

2. The block of claim 1 having at least two additional bores as described in (g).

* * * * *

UNITED STATES PATENT AND TRADEMARK OFFICE
CERTIFICATE OF CORRECTION

PATENT NO. : 4,495,945
DATED : January 29, 1985
INVENTOR(S) : Kenneth B. Liegner It is certified that error appears in the above-identified patent and that said Letters Patent are hereby corrected as shown below:

Col. 1, line 17; "by" should read -- of --

Col. 5, line 37; "marginal one" should read -- marginal zone --

Col. 6, line 46; "vertibulum" should read -- vestibulum --

Signed and Sealed this

Eighteenth Day of June 1985

[SEAL]

Attest:

DONALD J. QUIGG

Attesting Officer          Acting Commissioner of Patents and Trademarks